United States Patent [19]

Fisslinger

[11] Patent Number: 5,720,619
[45] Date of Patent: Feb. 24, 1998

[54] INTERACTIVE COMPUTER ASSISTED MULTI-MEDIA BIOFEEDBACK SYSTEM

[76] Inventor: Johannes Fisslinger, 520 Washington Blvd. #907, Marina del Rey, Calif. 90292

[21] Appl. No.: 427,556

[22] Filed: Apr. 24, 1995

[51] Int. Cl.$^6$ ................................................. A63F 9/22
[52] U.S. Cl. ........................................ 434/336; 434/350
[58] Field of Search .................... 364/413.01, 413.02, 364/413.03, 413.04, 413.05, 413.06, 413.13, 413.14, 413.15, 413.16, 413.17, 413.19, 514 A, 419.2; 128/700, 731, 732, 670, 905, 782; 434/321, 322, 336, 350

[56] References Cited

U.S. PATENT DOCUMENTS

| | | | |
|---|---|---|---|
| 5,024,235 | 6/1991 | Ayers | 128/732 |
| 5,132,714 | 7/1992 | Samon | 348/64 |
| 5,209,494 | 5/1993 | Spector | 273/431 |
| 5,213,338 | 5/1993 | Brotz | 128/731 |
| 5,253,168 | 10/1993 | Berg | 128/725 |
| 5,304,112 | 4/1994 | Mrklas et al. | 601/15 |
| 5,343,871 | 9/1994 | Bittman et al. | 128/732 |
| 5,362,049 | 11/1994 | Höfer | 128/632 |
| 5,447,166 | 9/1995 | Gevins | 128/731 |
| 5,465,729 | 11/1995 | Bittman et al. | 128/732 |
| 5,474,082 | 12/1995 | Junker | 128/732 |
| 5,571,057 | 11/1996 | Ayers | 128/782 |

FOREIGN PATENT DOCUMENTS

| | | |
|---|---|---|
| 4-325180 | 11/1992 | Japan. |
| 4-336091 | 11/1992 | Japan. |

Primary Examiner—Benedict V. Safourek
Assistant Examiner—Seema S. Rao
Attorney, Agent, or Firm—Richard C. Litman

[57] ABSTRACT

The present invention relates to an interactive computer-assisted, multi-media biofeedback system which displays a user's physiological data as a colored aura driving a computer video game or program. The system includes: (1) a personal computer processing unit with a color video monitor, (2) software programs to digitally generate a color aura portrait, alterable in real-time in response to the changes of measured physiological variables of the user, (3) a video game Biostick which measures the user's physiological variables and input control devices such as a mouse or keyboard, (4) audio components for auditory feedback, and (5) remote communications devices. Software may consist of competitive or educational exercises or adventures which are interactive with the user's physical skills of controlling a joystick and controlling the physiological variables as represented by the aura measured through the Biostick. An electronic computer input signal is received and processed by the cpu and a synchronized television broadcast signal viewed on a television set. Either the computer game's action sequences, television program output, or both, are affected by remote transmission of input data comprised of the user's physiological variables as measured by the Biostick. The variables change as the viewer is stimulated by the television action being watched. Viewing the changes in the aura allows a user to practice control of subconscious energies and alter both the computer and television output.

2 Claims, 2 Drawing Sheets

INTERACTIVE COMPUTER ASSISTED MULTI-MEDIA BIOFEEDBACK SYSTEM

BACKGROUND OF THE INVENTION

1. Field of the Invention

The present invention relates to an interactive computer-assisted, multi-media biofeedback system which displays a user's physiological data as a colored aura driving a video game or otherwise integrated into a computer program.

2. Description of the Prior Art

Biofeedback systems are known in the prior art to have been used to monitor and regulate physiological functions, and psychological or emotional behavior. Typically, various measuring devices translate physiological or other variables into a visual or auditory display, thereby allowing subconscious behavior of a subject-user to be monitored and regulated at a conscious level. Biofeedback methods have measured such variations in galvanic skin response (GSR), brain wave activity (electroencephalogram or EEG), cardiac neuroelectric potentials (electrocardiogram or EKG), muscular neuroelectric potentials (electromyogram or EMG), heart rate (pulse), blood gas values (carbon dioxide and oxygen levels), and body temperature. Aura recording devices measure physiological electrical potentials (usually of the hand) which are translated into an image (usually of the face) throughout which patterns of color emerge representing the user's aura. Regardless of the type variables used as input into the biofeedback system, the user then attempts to adjust those physiological variables in such a way as to alter the various sensory patterns displayed, thereby learning to control them.

U.S. Pat. No. 5,253,168 issued Oct. 12, 1993 to Berg discloses a computer based system for creative expression using biofeedback signals linked to direct imaging and audio devices. A user enters a computer by selecting from a predetermined set of software programs a desired art form of an individual's interest. A color video camera obtains a real time image of the user for display on a color computer video monitor. A graphics module is further coupled to a CPU to generate alterable video signals for driving the color video monitor. The CPU receives biofeedback from pulse, temperature, EKG, and EEG sensors attached to the user to alter the video signal driving the monitor and the resulting video display changes according to the biofeedback activity of the user.

U.S. Pat. No. 5,362,049 issued Nov. 8, 1994 to Hofer describes a computer game unit which is adapted to receive physiological values, such as pulse, blood gases and temperature. Normal game scores provided through the computer game during play are factored by these measured physiological values to reflect the effect of emotional or mental behavior in the score. The measured variables can alternatively be used to operate and control video game actions.

U.S. Pat. No. 5,132,714 issued Jul. 21, 1992 to Samon describes a portrait camera with an aura recording means using electrodes attached to the hand which alter the light and color image picked up the by the portrait camera. The electrodes are coupled to the camera by a microprocessing means.

U.S. Pat. No. 5,024,235 issued Jun. 18, 1991 to Ayers describes a system for displaying and either inhibiting or promoting selected bioelectrical frequencies emitted by a living organism. The system includes a pair of electrodes, an analog signal amplifier, an analog digital converter, a selector to select a frequency of interest, a display monitor, and a computer to distinguish the digital signals as different frequencies, display the frequencies, and determine when the frequency is falling inside or outside a predetermined range. U.S. Pat. No. 5,304,112 issued to Mrklas et al. discloses a light pattern stress level display which acts as a biofeedback stimulus which the user attempts to control by comparing it to a target display.

U.S. Pat. No. 5,209,494 issued May 11, 1993 to Spector describes a biofeedback game in which a target player is coupled by a temperature sensor on a fingertip to a biofeedback monitor. Provocative questions from predetermined categories are asked of the player and the player must attempt to maintain "his cool" by viewing the monitor in response to the question. U.S. Pat. No. 5,213,338 issued May 25, 1993 to Brotz describes a game having circuitry for conversion of brain wave intensity to direct the movement of rotation of a circular visual display. The game can be played by two players competing with one another.

Japanese Pat. No. 4-325180 issued to Hirose describes a game wherein the emotional changes of a player are measured by a visual display comprising a thermal infra-red and visible video image of the face. Fluctuations of the visual image in real time are compared with data in memory to determine the user's tension, which determines the difficulty of the game. Japanese Pat. No. 4-336091 issued to Wakayama describes, generally, a video game using virtual reality imaging.

However, the prior art fails to integrate an aura recording device with an interactive computer system so that the color of the aura dictates the subsequent course or outcome of the computer game or exercise program as described below. No one has integrated a computer program with an aura measuring device so that when the user's physiological variables (measured and displayed as the aura) are shown to the player, the player can not only regulate the colors of the aura, but can affect the output of the program in such a way that the programs are altered to reach a desired goal. By learning to control the aura color changes, the user can affect the game in a way to control the functions of the game.

None of the above referenced inventions and patents, taken either singly or in combination, is seen to describe the instant invention as claimed.

SUMMARY OF THE INVENTION

The present invention relates to an interactive computer, multi-media assisted biofeedback system which displays a user's physiological data as a colored aura driving a video game or otherwise integrated into a computer program. The system includes: (1) a personal computer processing unit with a color video monitor, (2) a software program, installed in the personal computer able to digitally generate a color aura portrait of a user which changes in real-time in response to the changes of measured physiological variables, such as electric potentials and body temperature, (3) a game joystick which acts as a biofeedback sensor (Biostick) for measuring the physiological variables for input into the video game so as to create the aura portrait, (4) audio components which allow auditory feedback to guide the user through the video exercises or game, and (5) remote communications devices, by which remote signals can be sent, received and inputted into a computer game or other program and may correspond to television signals broadcast for viewing on a television set.

The aura represents the image of the user, or other characters, and is created by a computer processing unit and a software program which processes physiological data input, such as galvanic skin response, EEG, EMG, etc., from the Biostick. The computer software may consist of exercises, lessons, pictures and adventures that are interactive with the physiological variables data input so as to create games of competitive or educational varieties. In addition, a video game's action sequences or other computer program's content can also be altered according to the variables affected by remote signals, which may be sent from a television broadcast facility. Alternatively, the user may send his aura data via remote communications devices such as the Internet to remote computer terminals for such uses as sending an aura profile through an on-line dating service. Through practice, a user may master skills of the subconscious mind and the body's energy which the biofeedback games emphasize.

Accordingly, it is an object of the present invention to provide a computer system whereby a software program can be installed on a personal computer to enable to digitally generate a color aura portrait of a user which changes in real-time in response to the changes of measured physiological variables.

It is another object of the present invention to provide a means of measuring a changing aura by use of a Biostick, which acts as a biofeedback sensor for measuring physiological variables for input variables into the video game so as to create the aura portrait.

It is a further object of the present invention to provide an interactive means by which the user can control the progress of an computer exercise program or video game by using biofeedback.

Still another object of the present invention is to provide a means of controlling a biofeedback game in which remote signals can be sent, received, and inputted into a computer program to interactively affect its outcome.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
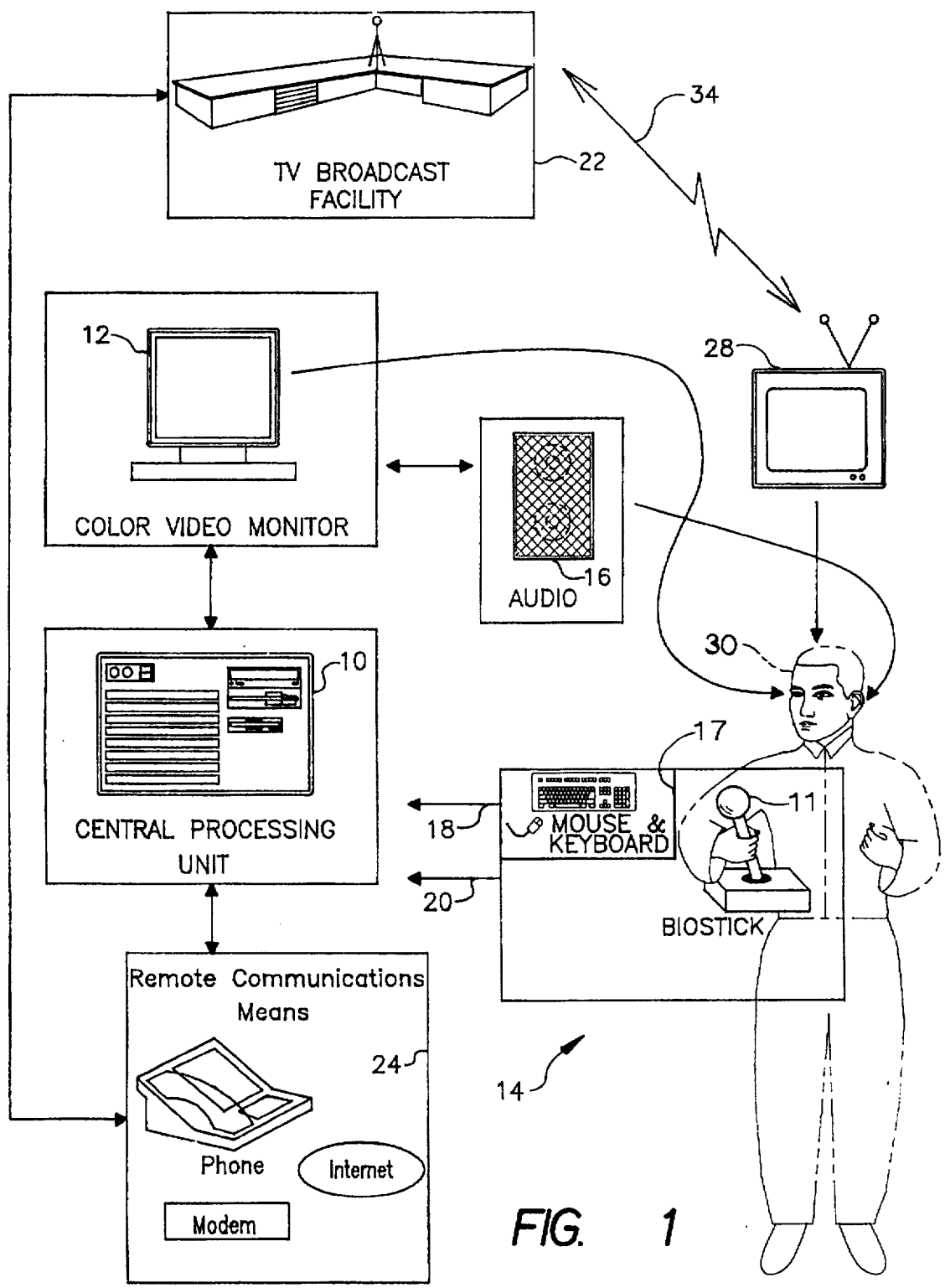
FIG. 1 is a diagrammatic representation in overview of the components of the system.

In the preferred embodiment of the present invention and referring to FIG. 1 of the drawings, the computer system includes a personal computer processing unit (cpu) 10 with a color video monitor 12, an input control mechanism 14, and an audio speaker 16. The cpu 10 may include any platform or personal computing device known in the prior art capable of handling graphics and video game software. The presently preferred software is CD-ROM with sufficient memory to hold the necessary programs for control of both an aura display on the video monitor, or other highly graphic video game programs. Each cpu 10 is installed with software which is designed to create an image of a user or other character altered by input variables measured directly from the user 30.

Figure 2:
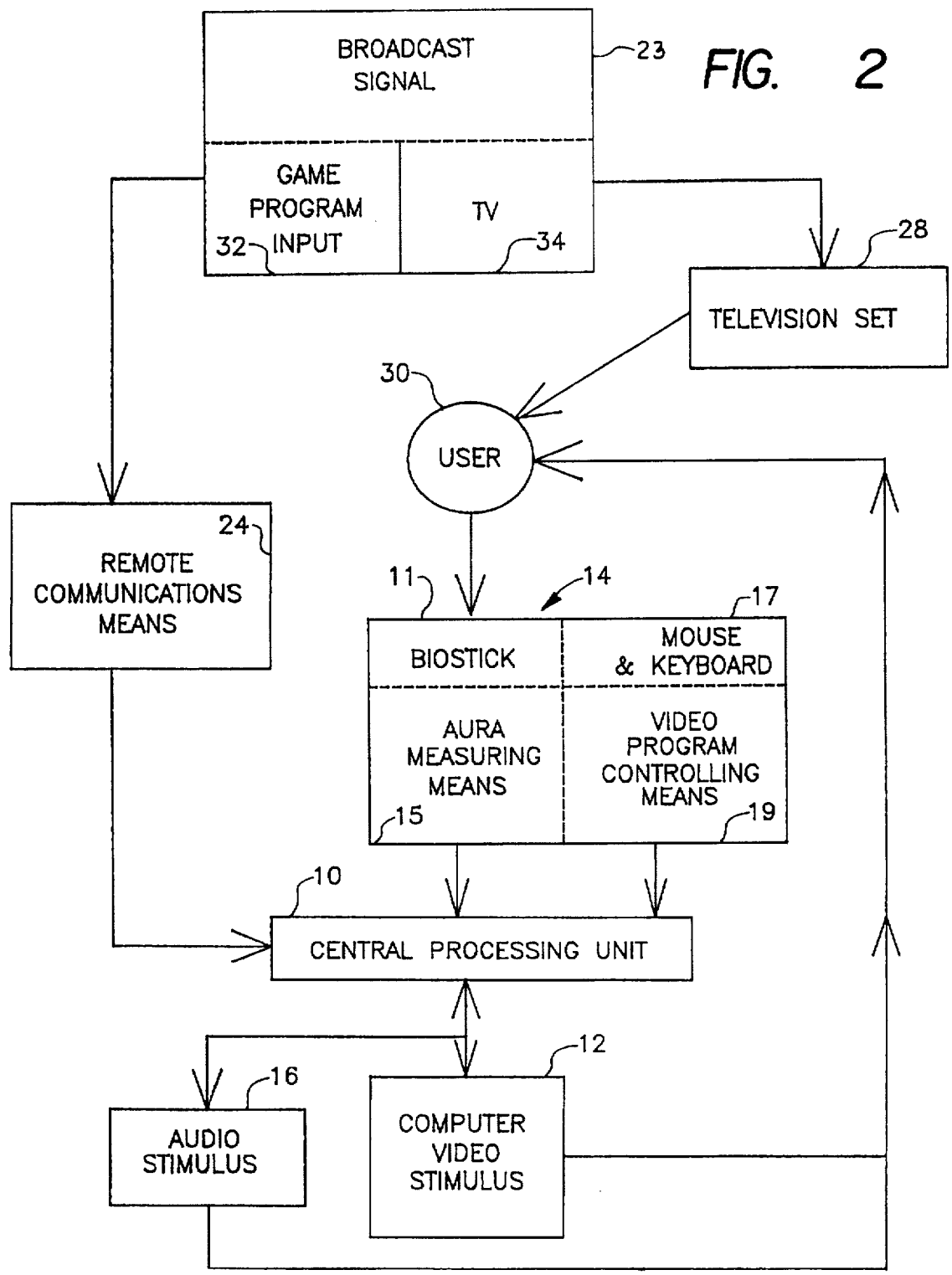
FIG. 2 is a block diagram of the components of the system.

Referring to both FIGS. 1 and 2, the input variables are controlled by the input control mechanism 14 comprising two components. First, control devices known in the prior art, such as a mouse or keyboard 17, control the video game or other predetermined computer program, as represented by the input arrow 18 in FIG. 1 and block 19 in FIG. 2. Second, the Biostick 11 is capable of measuring physiological variables of a user's body, as indicated by block 15 in FIG. 2. These two control devices may also be combined to create one unit which serves both input functions. These measured physiological variables are input into the video game or other program and provide the raw data needed to create the aura portrait, as represented by input arrow 20 in FIG. 1. Each software program installed onto the cpu 10 digitally generates a color aura of the whole or part of the body which changes in real-time in response to the changes of measured physiological variables of the hand as measured by the Biostick 11.

These means provide the basis for the biofeedback loop which allows the user to learn control over the colors and changes in the aura display as presented on the color video monitor 12. Depending on the software installed, the aura may be displayed in various formats. The representation of the user's aura on the video monitor 12 may be used at a first level to simply train the user to control his aura. This training is accompanied by a voice guiding the user softly speaking over an audio speaker 16 during the training. The voice is generated by the cpu 10, being processed according to the software program and coupled in response to the user's input.

If the user prefers, the user may substitute a competitive type of software program which generates a game by which a user must control his aura in order to reach preprogrammed goals. The goals may be in the form of controlling the actions of characters in the game or achieving other prizes or goals as set forth by the program. The user again controls the input by use of the Biostick Referring again to both FIGS. 1 and 2, the cpu 10 is also linked to a remote location, as represented by the television broadcasting facility 22, through the use of remote communications means 24, such as a modem using telephone communications lines, the Internet, cable television transmission or other devices. In the preferred embodiment, a signal is inputted and processed by the game program sent from a remote location so as to incorporate unknown information into the actively used program, and, whereby further a synchronized television signal is altered by return input to the broadcast facility from the user's actions upon the program.

The television broadcast facility 22 transmits signals either as individual signals or as a combined divisible signal, comprising a game program input signal 32 and a standard television signal 34. The game program input signal 32 is sent through the remote communications devices 24 directly to the cpu 10 to convey data which is received and inputted into the video game program. These data signals are synchronized with the television broadcast signal 34 being concurrently received and viewed by the user on a television signal receiving and viewing means, i.e. a personal television set 28. The two signals transmitted are synchronized so that the action of the video game program corresponds to the action seen on television. As the viewer watches the television action, the user must control his physiological variables being measured in such a way that he achieves a desired output on the video monitor 12, and concurrently on the television screen 28.

In this way, the game's action sequences are affected in three ways. First, the game program's output on the video monitor would be directly affected by the input of the remote signals transmitted to the cpu 10 for processing. These signals would partially affect or override the game program input 32 to control the game program. However, game program variables affected by the aura measuring means 15 would remain in the control of the user.

Second, the user himself or herself would also be affected by the stimulus of the program seen and heard on the television set 28. Depending on the amount of control exerted by the user over his or her aura during the effects of viewing the television set, the program output is altered accordingly by the input of the user's measured values.

Third, the user's physiological variables measured by the aura measuring means 15 may be transmitted back to the broadcast facility 22, or other remote location, to be processed so as to affect the television signal and thereby affect the broadcast viewed by the user. By these means, the user can challenge his ability to control his aura under external stimuli.

Another alternative includes the transmission of the input of the user's aura information over the Internet to a remote location where the user's aura would then be displayed for informational purposes. For example, in an on-line dating service setting, the aura may be viewed by the remote user and used much like a personality profile.

It is to be understood that the present invention is not limited to the embodiments described above, but encompasses any and all embodiments within the scope of the following claims.

I claim:

1. An interactive computer assisted multi-media biofeedback game for influencing a player's aura, comprising:
   a central processing unit installed with a software program for generating an alterable aura image of a player;
   an input control mechanism communicating with said central processing unit, said input control mechanism including a joystick for measuring physiological variables of the player;
   a color video monitor communicating with said central processing unit, said video monitor displaying in realtime the alterable aura of the player in response to changes in the player's physiological variables;
   an audio component communicating with said central processing unit, said audio component outputting a verbal instruction to the player for influencing the physiological variables;
   a modem communicating with said central processing unit for transmitting physiological variable data; and
   signal sending means for generating a remote signal received by said modem for input into said central processing unit.

2. The biofeedback game as defined in claim 1, wherein said signal sending means further includes a television signal in a synchronized transmission with said remote signal, said television signal being received by a television set for viewing by the player.

* * * * *